United States Patent [19]

Oyobe et al.

[11] Patent Number: 4,612,189

[45] Date of Patent: Sep. 16, 1986

[54] DENTIFRICE COMPOSITION

[75] Inventors: Masaaki Oyobe, Kanagawa; Hiromichi Ichikawa, Tokyo; Tsutomu Maeyama, Chiba, all of Japan

[73] Assignee: Lion Corporation, Tokyo, Japan

[21] Appl. No.: 372,005

[22] Filed: Apr. 26, 1982

Related U.S. Application Data

[63] Continuation of Ser. No. 179,795, Aug. 20, 1980, abandoned.

[30] Foreign Application Priority Data

Aug. 31, 1979 [JP] Japan .................. 54-111409

[51] Int. Cl.$^4$ ................................ A61K 7/16
[52] U.S. Cl. ........................................ 424/49
[58] Field of Search ............................ 424/49

[56] References Cited

U.S. PATENT DOCUMENTS

| | | | |
|---|---|---|---|
| 3,003,919 | 10/1961 | Broge | 424/49 |
| 3,836,641 | 9/1974 | Hoyles et al. | 424/49 |
| 3,864,470 | 2/1975 | Watson | 424/49 |
| 3,906,090 | 9/1975 | Colodney | 424/52 |
| 3,911,102 | 10/1975 | Harrison | 424/49 |
| 3,911,104 | 10/1975 | Harrison | 424/49 |
| 3,946,108 | 3/1976 | Tomlinson et al. | 424/49 |
| 4,036,949 | 7/1977 | Colodney | 424/49 |
| 4,066,745 | 1/1978 | Tomlinson et al. | 424/49 |

FOREIGN PATENT DOCUMENTS

| | | |
|---|---|---|
| 1348492 | 4/1971 | United Kingdom . |
| 1349373 | 4/1971 | United Kingdom . |
| 1347650 | 4/1974 | United Kingdom . |
| 1400153 | 7/1975 | United Kingdom . |
| 1433743 | 4/1976 | United Kingdom . |

*Primary Examiner*—Donald B. Moyer
*Assistant Examiner*—C. Joseph Faraci
*Attorney, Agent, or Firm*—Birch, Stewart, Kolasch & Birch

[57] ABSTRACT

Transparent and translucent dentifrice compositions improved in cleaning ability, stain removing ability and feeling are disclosed which comprise a mixture of an amorphous silica and an amorphous silicate containing at least 70% by weight of $SiO_2$ which is partially interbonded with 1-10% by weight of an oxide of a metal selected from the group consisting of aluminum, magnesium and calcium and a transparent vehicle having substantially the same refractive index as that of the silica, the ratio of the silica to the silicate being in the range of 4:6 to 6:4 on a weight basis, the content of said mixture being in the range of 1 to 25% by weight of the composition, and the pH of the composition being in the range of 4.5 to 10.

2 Claims, No Drawings

DENTIFRICE COMPOSITION

This application is a continuation of copending application Ser. No. 179,795, filed on Aug. 20, 1980, now abandoned.

BACKGROUND OF THE INVENTION

This invention relates to translucent and transparent dentifrice compositions with optimum abrasiveness and favorable feeling.

In general, translucent or transparent dentifrices are prepared by admixing a humectant, a binder and other ingredients with water to provide a transparent vehicle having a refractive index of 1.40–1.47 and blending the vehicle and an amorphous silica-family abrasive having substantially the same refractive index as that of the vehicle. As the silica-family abrasive for translucent or transparent dentifrices, anhydrous or hydrated amorphous silicas are usually used. Anhydrous or hydrated amorphous silicates such as sodium or potassium aluminosilicates in which $SiO_2$ is inter-bonded with 1–10% by weight of alumina, magnesia or other metal oxides are also used. U.S. Pat. Nos. 3,836,641, 3,864,470, 3,906,090, 3,911,102, 3,911,104, 3,946,108, 4,036,949 and 4,066,745 and British Pat. Nos. 1,348,492, 1,349,373, 1,347,650, 1,400,153 and 1,433,743 disclose various silica-family abrasives.

Through a series of experiments, the inventors have found that amorphous silicas in which $SiO_2$ is partially inter-bonded with less than 1% by weight of metal oxide give highly transparent dentifrices, but have poor abrasiveness and stain removal. Crystalline silicas can satisfy abrasiveness, but will harm the tooth surface because they are not available in fine particles. On the other hand, amorphous silicates bring about less transparent dentifrices as compared with amorphous silicas. Moreover, a humectant having a high refractive index such as glycerine or sorbitol must be blended in a larger amount because the amorphous silicates have relatively high refractive indexes. The dentifrices containing such a larger amount of the humectant have unfavorable taste and feeling.

Accordingly, the prior arts of translucent and transparent dentifrices are more or less impractical since problems remain with respect to abrasiveness, feeling and stand-up quality.

SUMMARY OF THE INVENTION

An object of the present invention is to provide substantially transparent and translucent dentifrice compositions having optimum abrasiveness, good stain removing ability and favorable feeling.

According to this invention, there is provided a dentifrice composition comprising a mixture of an amorphous silica and an amorphous silicate containing at least 70% by weight of $SiO_2$ which is partially inter-bonded with 1 to 10% by weight of an oxide of a metal selected from the group consisting of aluminum, magnesium and calcium, and a transparent vehicle having substantially the same refractive index as that of the silica, the ratio of the silica to the silicate being in the range of 4:6 to 6:4 on a weight basis, the content of said mixture being in the range of 1 to 25% by weight of the composition, and the pH of the composition being in the range of 4.5 to 10.

It has been generally believed that a mixture of a silica and a silicate would not result in a highly transparent dentifrice composition because of the difference in refractive indexes between the silica and the silicate. Unexpectedly, the inventors have found that a transparent or translucent dentifrice composition having optimum abrasiveness, improved stain removal ability and favorable feeling can be obtained by using as the abrasives an amorphous silica and an amorphous silicate containing at least 70% by weight of $SiO_2$ which is partially inter-bonded with 1 to 10% by weight of alumina, magnesia or calcium oxide, admixing the silica and the silicate at a relative proportion of 4:6 to 6:4 on a weight basis, and blending this mixture with a transparent vehicle having substantially the same refractive index as that of the silica so that the mixture of the silica and the silicate is present in the range of 1 to 25%, preferably 5 to 15% by weight of the composition.

Preferably the abrasive mixture of a synthetic, hydrated, amorphous silica having an average particle size of 0.5–30 microns, a specific surface area (BET method) of not more than 500 $m^2/g$, a refractive index of 1.44–1.47, a liquid absorption of 0.8–1.3 c.c./g, and $SiO_2$ content of at least 70% by weight, preferably more than 90% by weight and a synthetic, hydrated, amorphous silicate having an average particle size of 0.5–30 microns, a specific surface area (BET method) of not more than 500 $m^2/g$, a refractive index of 1.445–1.47, and a liquid absorption of 0.6–1.2 c.c./g gives transparent and translucent dentifrices having more favorable feeling and improved stand-up quality comparable or superior to conventional dentifrices containing dicalcium phosphate dihydrate as the abrasive. Particularly when an aluminosilicate containing 1–5% by weight of $Al_2O_3$ is combined with the above-defined silica, the resulting dentifrice has an extremely high degree of transparency.

The above and other objects, features and advantages of this invention will become more apparent and understandable from the Detailed Description, Examples and Claims.

DETAILED DESCRIPTION OF THE INVENTION

The dentifrice composition of this invention comprises a mixture of an amorphous silica and an amorphous silicate as abrasives and a vehicle having substantially the same refractive index as that of the silica.

The silicas which can be used herein include amorphous silicas such as precipitated silicas, silica xerogels and silica aerogels. Precipitated silicas are most preferred since the resulting dentifrices have good stand-up quality. The preferable silicas have an $SiO_2$ content of at least 70% by weight, more preferably more than 90% by weight, an alkali and alkaline earth metal oxide content of 0–5% by weight, more preferably 0–2% by weight (the content of the inter-bonded metal oxides is less than 1%), an adhesive moisture content (loss on drying) of 1–10% by weight, an average particle size of 0.5–30 microns, more preferably 1–15 microns, a specific surface area (BET method) of not more than 500 $m^2/g$, more preferably not more than 300 $m^2/g$, a refractive index of 1.44–1.47, and a liquid absorption of 0.8–1.3 cc./g.

Illustrative of the silicas are such commercial products as being available under the tradenames, Zeodent 113 (J. M. Huber Corporation, U.S.A.) and Syloid 63 (W. R. Grace Company, U.S.A.).

The silicates which can be used herein include amorphous silicates synthesized by liquid process such as precipitated silicates and silicate xerogels. Most preferred are precipitated silicates.

In the present invention, the silicates contain at least 70% by weight of $SiO_2$ which is partially interbonded with 1-10% by weight of an oxide of a metal selected from aluminum, magnesium and calcium. The silicates containing less than 1% by weight of the metal oxide result in poor abrasiveness and unfavorable feeling. The silicates in which $SiO_2$ is inter-bonded with more than 10% by weight of the metal oxide reduce the degree of transparency of the dentifrice and increase their refractive indexes, resulting in unfavorable taste and feeling because a humectant of a high refractive index such as glycerin must be used in a larger amount. Moreover, when metal oxide contents exceed 10% by weight, abrasiveness becomes too excessive. The most preferable silicates are aluminosilicates in which $SiO_2$ is partially inter-bonded with 1-5% by weight of $Al_2O_3$. The aluminosilicates bring about highly transparent dentifrices having good cleaning ability and feeling.

The preferable silicates have an adhesive moisture content (loss on heating) of 1-10% by weight, an average particle size of 0.5-30 microns, more preferably 1-15 microns, a specific surface area (BET method) of not more than 500 $m^2/g$, more preferably not more than 300 $m^2/g$, a refractive index of 1.445-1.47, and a liquid absorption of 0.6-1.3 c.c./g.

Illustrative of the silicates are such commercial products as being available under the tradenames, Zeo 49 (J. M. Huber Corporation, U.S.A.), Sident 20 (Deutsche Gold-und Silber-Scheideanstalt, West Germany) and Britesorb 90 (Philadelphia Quartz Company, U.S.A.).

According to this invention, the silica and the silicate are mixed in a ratio of 4:6 to 6:4 on a weight basis. Within this range, the resulting dentifrice compositions are excellent in transparency, cleaning ability and feeling. Reduced transparency and excessive abrasiveness will result from lower ratios of the silica to the silicate, i.e. higher ratios of the silicate to the silica, whereas poor abrasiveness, poor stain removing ability and unfavorable feeling will result from higher ratios of the silica to the silicate, i.e. lower ratios of the silicate to the silica.

The content of the mixture of the silica and the silicate is in the range of 1-25% by weight, preferably 5-15% by weight of the composition. Within the above-defined contents of the mixture, dentifrices having allowable transparency, optimum abrasiveness and favorable feeling can be obtained. If the mixture of the silica and the silicate is blended in amounts exceeding the upper limit, that is, 25% by weight, the resulting dentifrices will have excessive abrasiveness, reduced transparency and unfavorable feeling.

The dentifrice compositions of the present invention are prepared by blending the silica and the silicate at the above-defined ratio and content to a transparent vehicle having substantially the same refractive index as that of the silica. By substantially matching the refractive index of the transparent vehicle to that of the silica, transparent or translucent dentifrices can be obtained irrespective of the difference in the refractive indexes between the silica and the silicate.

The transparent vehicle which can be used in the dentifrice composition of this invention may include well-known ingredients which are used in conventional dentifrices. The transparent vehicle may be prepared by mixing a humectant, a binder and a surfactant with water. The humectant includes glycerine, sorbitol, propylene glycol, polyethylene glycol, xylitol and the like. The content of the humectant is about 40-80%, preferably 50-70% by weight. The binder includes carrageenan, sodium alginate, sodium carboxymethyl cellulose, methyl cellulose, hydroxypropyl cellulose, hydroxyethyl cellulose, polyvinyl pyrrolidone, tragacanth gum, karaya gum, xanthane gum, sodium polyacrylate, bentonite and the like. The content of the binder is about 0.1-5%, preferably 0.3-3% by weight. The surfactant includes anionic surfactant, for example, higher alkyl sulfates such as sodium lauryl sulfate, acyl sarcosinates such as sodium lauryl sarcosinate, higher-fatty acid monoglyceride monosulfates, higher alkyl aryl sulfonates, olefin sulfonates, acyl glutamates and the like, and nonionic surfactants, for example, alkyrol diethanol amides such as lauroyl diethanol amide, sucrose fatty acid esters such as sucrose monolaurate and dilaurate, hardened castor oil derivatives, higher fatty acid monoglycerides such as stearic acid monoglyceride, Pluronic agents and the like. The content of the surfactant is about 0.1-5%, preferably 0.5-2% by weight. The vehicle may further include a sweetner such as sodium saccharin, glycyrrhizinic acid and its salt, stevioside, neohesperiden dihydrochalcone, perillartine, p-methoxycinnamic aldehyde and the like in an amount of 0 to 2%, preferably 0.1 to 1%, a flavor such as l-menthol, anethole, carvone, speamint oil, pepermint oil, etc. in an amount of 0.1 to 7%, preferably 0.5 to 2%; an antiseptic agent such as butyl or methyl parahydroxybenzoate, etc.; and other effective ingredients such as sodium fluoride, sodium monofluorophosphate, stannous fluoride, chlorohexidine hydrochloride, chlorohexidine gluconate, disodium hydrogen phosphate, glycerophosphate compound, $\epsilon$-aminocaproic acid, tranexamic acid, aluminum chlorohydroxyallantoinate, dextranase, mutanase sodium chloride, etc. Toothpastes may be prepared in a conventional manner.

The dentifrice composition of this invention may include in addition to the silica and the silicate, a pyrogenic, ultrafine, anhydrous silica as well as conventional abrasives such as dicalcium phosphate dihydrate and aluminum hydroxide in amounts causing no adverse effect on transparency.

The dentifrice compositions according to this invention may generally have a pH of 4.5 to 10, preferably 6 to 8.5.

In order to more fully and clearly illustrate the present invention, the following examples are presented which should be considered as illustrative rather than limiting the invention disclosed and claimed herein. Comparative examples are also presented to demonstrate improvements by the present invention. All percents are by weight.

EXAMPLES 1-9 AND COMPARATIVE EXAMPLES 1-4

Using synthetic, amorphous, hydrated, precipitated silica specified in Table 1 and synthetic, amorphous, hydrated, precipitated silicates specified in Table 2, toothpastes having formulations shown in Table 3 were prepared in an ordinary manner.

These toothpastes were tested for transparency, cleaning ability and feeling. The results are shown in Table 3.

TABLE 1

| Properties of Silica | |
|---|---|
| $SiO_2$ content | 98.1% |
| $Na_2O$ content | 0.37% |

TABLE 1-continued

| Properties of Silica | |
|---|---|
| Al$_2$O$_3$ content | 0.70% |
| Moisture content (dried at 105° C. for 2 hours) | 7.96% |
| Average particle size | 6.8 microns |
| Refractive index | 1.454 |
| Liquid absorption | 0.90 c.c./g |

TABLE 2

| Properties of Silicate | CE1 | E1 | E2 | E3 | E4 | CE2 | E5 | E6 | E7 | E8 | CE3 | CE4 | E9 |
|---|---|---|---|---|---|---|---|---|---|---|---|---|---|
| SiO$_2$ content, % | 88.5 | 88.4 | 88.2 | 88.0 | 87.0 | 80.0 | 88.2 | 88.2 | 88.0 | 88.0 | 88.0 | 88.0 | 88.2 |
| Al$_2$O$_3$ content, % | 0.5 | 1.0 | 3.0 | 5.0 | 7.0 | 15.0 | 3.0 | 3.0 | 5.0 | 5.0 | 5.0 | 5.0 | — |
| MgO content, % | — | — | — | — | — | — | — | — | — | — | — | — | 3.0 |
| Na$_2$O content, % | Nil | 0.20 | 0.50 | 1.15 | 4.8 | 9.8 | 0.50 | 0.50 | 1.15 | 1.15 | 1.15 | 1.15 | 0.32 |
| Moisture content (105° C., 2 hours), % | 6.6 | 6.1 | 5.71 | 5.20 | 5.00 | 4.8 | 5.71 | 5.71 | 5.20 | 5.20 | 5.20 | 5.20 | 6.2 |
| Average particle size, μ | 5.0 | 6.3 | 4.4 | 6.8 | 8.6 | 8.0 | 4.4 | 4.4 | 6.8 | 6.8 | 6.8 | 6.8 | 9.0 |
| Specific surface area, m$^2$/g | 230 | 210 | 190 | 165 | 150 | 120 | 190 | 190 | 165 | 165 | 165 | 165 | 175 |
| Refractive index | 1.46 | 1.46 | 1.46 | 1.46 | 1.46 | 1.47 | 1.46 | 1.46 | 1.46 | 1.46 | 1.46 | 1.46 | 1.46 |
| Liquid absorption, cc/g | 1.3 | 1.10 | 0.95 | 0.88 | 0.72 | 0.62 | 0.95 | 0.95 | 0.88 | 0.88 | 0.88 | 0.88 | 0.98 |

TABLE 3

| | CE1 | E1 | E2 | E3 | E4 | CE2 | E5 | E6 | E7 | E8 | CE3 | CE4 | E9 |
|---|---|---|---|---|---|---|---|---|---|---|---|---|---|
| Silica (%) | 5.0 | 5.0 | 5.0 | 5.0 | 5.0 | 5.0 | 4.0 | 8.0 | 4.0 | 6.0 | 2.0 | 8.0 | 4.0 |
| Silicate | 5.0 | 5.0 | 5.0 | 5.0 | 5.0 | 5.0 | 4.0 | 8.0 | 6.0 | 4.0 | 8.0 | 2.0 | 4.0 |
| Pyrogenic ultrafine silica | 1.5 | 2.0 | 2.0 | 2.0 | 2.3 | 2.5 | 3.0 | 0.5 | 2.0 | 2.0 | 3.0 | 3.0 | 2.0 |
| Glycerine | 25.0 | 25.0 | 25.0 | 25.0 | 28.0 | 30.0 | 25.0 | 23.0 | 25.0 | 25.0 | 25.0 | 25.0 | 25.0 |
| 70% sorbitol | 44.0 | 44.0 | 44.0 | 44.0 | 42.0 | 41.0 | 45.0 | 41.0 | 44.0 | 44.0 | 45.0 | 45.0 | 54.7 |
| Polyethylene glycol | 10.0 | 10.0 | 10.0 | 10.0 | 10.0 | 10.0 | 10.0 | 10.0 | 10.0 | 10.0 | 10.0 | 10.0 | — |
| Sodium carboxymethyl cellulose | 0.6 | 0.6 | 0.7 | 0.7 | 0.7 | 0.7 | 0.7 | 0.7 | 0.7 | 0.7 | 0.8 | 0.8 | 0.9 |
| Sodium lauryl sulfate | 1.5 | 1.5 | 1.5 | 1.5 | 1.5 | 1.5 | 1.5 | 1.5 | 1.5 | 1.5 | 1.5 | 1.5 | 1.5 |
| Sodium saccharin | 0.1 | 0.1 | 0.1 | 0.1 | 0.1 | 0.1 | 0.1 | 0.1 | 0.1 | 0.1 | 0.1 | 0.1 | 0.1 |
| Flavor | 1.0 | 1.0 | 1.0 | 1.0 | 1.0 | 1.0 | 1.0 | 1.0 | 1.0 | 1.0 | 1.0 | 1.0 | 1.0 |
| Water | balance | balance | balance | balance | balance | balance | balance | balance | balance | balance | balance | balance | balance |
| Total (%) | 100 | 100 | 100 | 100 | 100 | 100 | 100 | 100 | 100 | 100 | 100 | 100 | 100 |
| Transparency | 5 | 5 | 5 | 5 | 4 | 3 | 5 | 4 | 4 | 5 | 2 | 5 | 3 |
| Cleaning ability | 1 | 2 | 2 | 2 | 2 | 3 | 2 | 3 | 3 | 2 | 3 | 1 | 2 |
| Feeling | o | o | o | o | o | x | o | Δ | o | o | o | Δ | o |
| Total evaluation | x | o | o | o | o | x | o | Δ | o | o | x | x | o |

Notes:
(1) Pyrogenic ultrafine silica
average particle size: 16 millimicrons;
specific surface area (BET method): 200 m$^2$/g;
SiO$_2$ content: more than 99.8%;
Al$_2$O$_3$ content: less than 0.05%;
H$_2$O content: less than 1%.
(2) Grades for the evaluation of transparency
5: transparent; O.D.$^{535 nm}_{5 mm}$ not more than 0.25
4: transparent, but slightly turbid; " 0.25*–0.4
3: translucent; " 0.4*–0.55
2: slightly transparent; " 0.55*–0.75
1: opaque; " more than 0.75
*Lower limits are all exclusive. The absorbance of the toothpaste in a cubic cell having 5 mm dick was measured at 535 nm.
(3) Grades for the evaluation of cleaning ability
3: RDA value 80 or more
2: RDA value 50–80
1: RDA value 50 or less
(4) Evaluation of feeling
Feeling tests using 1.5 g of toothpaste of the samples with 6 panels.
Control is 1.5 g of a toothpaste containing 50% by weight of dicalcium phosphate dihydrate.
o: comparable or superior to the control.
Δ: inferior to the control, but acceptable.
x: inferior to the control, and unacceptable.
(5) Total comprehensive evaluation
o: excellent in transparency, cleaning ability and feeling; very suitable as transparent dentifrices
Δ: good in transparency and cleaning ability, but poor in feeling; acceptable as transparent dentifrices
x: poor in either transparency or cleaning ability; unacceptable as transparent dentifrices (agglomerated particle)
Specific surface area (BET method) 125 m$^2$/g The results of Table 3 reveal that all the dentifrice compositions (toothpastes) of the present invention have a good transparent or translucent appearance, optimum abrasiveness and favorable tasting and feeling. Low transparency and excessive abrasiveness were found in toothpastes using a silicate with an excessively high $Al_2O_3$ content (Comparative Example 2) and toothpastes having an excessively high ratio of silicate to silica (Comparative Example 4). Cleaning ability was insufficient in toothpastes having an excessively low ratio of silicate to silica (Comparative Example 5).

What is claimed is:

1. A dentifrice composition having a transparent appearance, comprising:
   (a) an abrasive amorphous hydrated precipitated silica, having an $SiO_2$ content of at least 90% by weight, an alkali and alkaline earth metal oxide content of 0–5% by weight and an inter-bonded metal oxide content of less than 1% by weight, and having an average particle size of 0.5–30 microns, a specific surface area measured by the BET method of not more than 500 $m^2/g$, a refractive index of 1.44–1.47 and a liquid absorption of 0.8–1.3 c.c./g;
   (b) an amorphous precipitated silicate, containing at least 70% by weight of $SiO_2$ which is partially inter-bonded with 1 to 5% by weight of alumina, and having an average particle size of 0.5–30 microns, a specific surface area measured by the BET method of not more than 500 $m^2/g$, a refractive index of 1.445–1.47 and a liquid absorption of 0.6–1.2 c.c./g; and
   (c) a transparent vehicle having substantially the same refractive index as that of the silica, the ratio of the silica to the silicate being in the range of 4:6 to 6:4 on a weight basis, the content of the mixture of the silica and the silicate being in the range of 5 to 15% by weight of the composition, and the pH of the composition being in the range of 4.5 to 10.

2. A dentifrice composition having a transparent appearance, comprising:
   (a) an abrasive amorphous hydrated precipitated silica, having an $SiO_2$ content of at least 90% by weight, an alkali and alkaline earth metal oxide content of 0–5% by weight and an inter-bonded metal oxide content of less than 1% by weight, and having an average particle size of 0.5–30 microns, a specific surface area measured by the BET method of not more than 500 $m^2/g$, a refractive index of 1.44–1.47 and a liquid absorption of 0.8–1.3 c.c./g;
   (b) an amorphous precipitated silicate, containing at least 70% by weight of $SiO_2$ which is partially inter-bonded with 1 to 10% by weight of alumina, and having an average particle size of 0.5–30 microns, a specific surface area measured by the BET method of not more than 500 $m^2/g$, a refractive index of 1.445–1.47 and a liquid absorption of 0.6–1.2 c.c./g; and
   (c) a transparent vehicle having substantially the same refractive index as that of the silica, the ratio of the silica to the silicate being in the range of 4:6 to 6:4 on a weight basis, the content of the mixture of the silica and the silicate being in the range of 5 to 15% by weight of the composition, and the pH of the composition being in the range of 4.5 to 10.

* * * * *